(12) United States Patent
Murthy (10) Patent No.: US 9,796,161 B2
(45) Date of Patent: Oct. 24, 2017

(54) DISPOSABLE CARD BARRIER ASSEMBLY FOR PERSONAL SKIN HYGIENE

(71) Applicant: Tallamraju V Murthy, Nashua, NH (US)

(72) Inventor: Tallamraju V Murthy, Nashua, NH (US)

(73) Assignee: TALLAMRAJU MURTHY, Nashua, NH (US)

( * ) Notice: Subject to any disclaimer, the term of this patent is extended or adjusted under 35 U.S.C. 154(b) by 0 days.

(21) Appl. No.: 14/833,110

(22) Filed: Aug. 23, 2015

(65) Prior Publication Data
US 2017/0051183 A1    Feb. 23, 2017

(51) Int. Cl.
| | | |
|---|---|---|
| C09J 7/02 | (2006.01) |
| B32B 29/00 | (2006.01) |
| B32B 9/04 | (2006.01) |
| B32B 7/06 | (2006.01) |
| B32B 7/12 | (2006.01) |

(52) U.S. Cl.
CPC ............ *B32B 29/002* (2013.01); *B32B 7/06* (2013.01); *B32B 7/12* (2013.01); *B32B 9/045* (2013.01); *B32B 2307/7145* (2013.01); *B32B 2425/00* (2013.01); *B32B 2571/00* (2013.01)

(58) Field of Classification Search
CPC .......... Y10T 428/14; C09J 7/026; B32B 7/06; B32B 7/12; B32B 9/045; B32B 29/002; B32B 2307/7145; B32B 2425/00; B32B 2571/00
See application file for complete search history.

(56) References Cited

U.S. PATENT DOCUMENTS

| | | | |
|---|---|---|---|
| 5,636,406 A | 6/1997 | Strong | |
| 5,799,331 A | 9/1998 | Stewart | |
| 6,178,554 B1 | 1/2001 | Pake | |
| 6,243,868 B1 | 6/2001 | Wanzenried | |
| 6,261,668 B1 * | 7/2001 | Nagy | A47B 77/022 428/194 |
| 6,647,549 B2 | 11/2003 | McDevitt | |
| 8,261,938 B2 | 9/2012 | Oradini, Sr. | |
| 8,294,585 B2 | 10/2012 | Barnhill | |
| 8,337,633 B2 | 12/2012 | Stine | |
| 8,602,257 B2 | 12/2013 | Godsell | |
| 8,684,228 B2 | 4/2014 | Parker | |
| 8,695,152 B2 | 4/2014 | Lemchen | |
| 8,752,213 B2 | 6/2014 | Schrecongost | |
| 9,003,568 B2 | 4/2015 | Hofmeister | |
| 2004/0083530 A1 | 5/2004 | LeVert | |

(Continued)

*Primary Examiner* — Patricia L Nordmeyer (57) ABSTRACT

The invention is a paper based card with an assembly of adhesive sheet, barrier strip and wax paper that is utilized to minimize transfer of particles between individuals and object surfaces. A disposable strip in the assembly, upon wear, adheres to the skin and serves as a barrier to minimize transfer of particles. This low cost invention is stackable, easy to carry, suited for routine use and facilitates easy wear of the barrier strip by placing selective regions of the palm on the cards. The invention complements other common methods such as hand washing and hand sanitizing which are routinely used to maintain hygiene and differentiates itself from other related inventions. The strips after wear promote hygiene and minimize direct contact with particles, thus addressing some of the limitations of the existing methods.

8 Claims, 6 Drawing Sheets

(56) References Cited

U.S. PATENT DOCUMENTS

| | | |
|---|---|---|
| 2006/0059663 A1 | 3/2006 | D'Ambrosio |
| 2007/0245850 A1* | 10/2007 | Ramali .................. A47B 95/02 74/551.9 |
| 2009/0162583 A1* | 6/2009 | Goodwin ............... A61B 50/30 428/34.1 |
| 2012/0148778 A1* | 6/2012 | Dawkins .............. A43B 17/102 428/40.1 |
| 2014/0078118 A1 | 3/2014 | Robb |
| 2014/0215676 A1 | 8/2014 | Jones |

* cited by examiner

DISPOSABLE CARD BARRIER ASSEMBLY FOR PERSONAL SKIN HYGIENE

BACKGROUND OF THE INVENTION

Field of Invention

The present invention relates to using a paper based card (referred to as Sanicard) to maintain skin hygiene in daily life especially on objects that are contacted my multiple individuals. The utility of the invention is to protect oneself from transfer of germs and contaminants from handshakes and other objects that come in contact with skin in everyday life.

Definition of Terms a) Particle: A particle in general is defined as a substance that occupies volume and possesses mass. Based on the size, the particles may be micro particles or nano particles and so on. In the context of the current invention, particles referred here include but are not limited to dirt, microbes, dust, food, body fluid droplets from sweat, nasal fluids, saliva, body salts, harmful substances in minute amounts (typically sub micro or nano amounts). b) Barrier strips: Barrier strips in relevance to this invention are strips of adhesive membrane that act as a barrier between the skin and the object surface. They can be made of different types of material and are preferably thin, microporous and breathable.

Transfer of unwanted and unhygienic particles, such as dust, microbes, food crumbs, and body fluids routinely occurs in our daily lives. This transfer which routinely occurs by touch, can lead to a variety of infections and is also unhygienic (Kimberly Parker, U.S. Pat. No. 8,684,228, 2009; Williams, C. K. and Carnahan, H. 2013). There are many locations in the body that are prone to exposure of unhygienic conditions. Skin hygiene, particularly of hands is considered to be one of the primary mechanisms to reduce risk of transmission of infectious agents by both contact and fecal-oral routes (Elaine Larson, 2001). Hand hygiene and finger hygiene have been extensively studied over the past several years in relation to locations where sterile conditions are important, such as hospitals and medical laboratories (Williams, C. et al. 2011). A variety of procedures, protective equipment and monitoring devices have been introduced and improved over years (Williams, C. K. and Carnahan, H. 2013). However, limitations still exist. The available methods or procedures may not be readily applicable in every situation, or are cumbersome or expensive to use and/or practice in daily lives. Hand washing with soap still remains the most common way to maintain hygiene and protect from particle transfer in day to day activities. There are other physical and chemical ways to prevent this transfer, such as, using protective barriers like gloves or via chemical methods like sanitizers (hand sanitizers) and sanitizing wipes. While there are different ways to prevent transfer of particles and maintain hygiene, there are limitations to every method and no single method is complete or always practical or feasible in daily life (Moore, G. 2013). For example, washing hands may not always be possible or practiced adequately in public places (Kimberly Parker, U.S. Pat. No. 8,684,228, 2009). Likewise, wearing gloves or masks on a regular basis for everyday tasks can be cumbersome and not practical. Moreover washing hands and using hand sanitizers can offer protection for a limited time, but do not eliminate or minimize direct contact of skin with particles. The necessity to have some sort of cover to protect the palm hence becomes obvious. In order to improve hygiene and protect palms, several devices/methods/approaches to produce and use finger gloves, hand covers, finger covers, mitts, finger protectors or disposable gloves have been reported (Hofineister, K. U.S. Pat. No. 9,003,568, 2015; Oradini, Sr. and Michael, E. U.S. Pat. No. 8,261,938,2012; Duffy, Timothy, US Patent 20090013441, 2007; Wanzenreid, Ernest, U.S. Pat. No. 6,243,868, 1999; Pake, C. W. et al. U.S. Pat. No. 6,178,554, 1998; Stewart, G. J. U.S. Pat. No. 5,799,331, 1998; Strong, Vonda, U.S. Pat. No. 5,636,406, 1997). The need for protection is obvious but the functionality of the product and ease of use are two main relevant and important issues covered in these inventions. Each of these inventions or methods have their own merits and demerits. Some of the referenced inventions that are suitable for fingers and finger tips may not be applicable for other regions of the palm. In light of these several inventions, it is evident that a variety of such inventions and innovative approaches are indeed needed to offer a practical choice for different needs and situations. Despite all the different available methods, particles rapidly spread between individuals on a routine basis and there is no single product or method that can address all issues. The reasons for this spread are because the existing procedures are insufficient, not taken seriously by individuals or not practiced adequately. This inertia to practice hygiene demands that any product or procedure suggested for hygiene needs to be effective, inexpensive, transportable, and simple enough to use and practice. Best hygiene practices are often achieved by incorporating various methods and complement each other (Patrick Stine, U.S. Pat. No. 8,337,633, 2012).

The invention presented here is a paper based card (referred to as Sanicard) that contains an adhesive sheet barrier assembly. A user uses the Sanicard to wear a barrier that minimizes transfer of particles between skins of individuals and object surfaces. The barrier is usually in a shape and size that covers the maximum surface that comes in contact with a surface of a particular application. The barrier can be removed using a rough surface present on the Sanicard. Sanicards can be in different sizes and shapes, but are usually small in size that can be stacked and carried around easily. The invention primarily focusses on palm hygiene but is also applicable to other parts of the body. The Sanicard differentiates itself from existing related inventions via its card based barrier assembly. As discussed in several of the patents listed, ease of use is one of the important features of having a product for hygiene. This card based assembly uses an adhesive barrier mechanism, but does not use an open or closed end method of wear as presented in other inventions (Oradini, Sr. and Michael, E. U.S. Pat. No. 8,261,938, 2012; Robb, Stephen, 20140078118 A1, 2014). Hence, this approach allows use of cards with a variety of dimensions and shapes that can cover several regions of the palm including fingers and other parts of the skin. Moreover, the card based approach also facilitates easy stacking and does not need any separate dispensing device. The card further facilitates wearing of barrier strips on all the digits in one instance thus reducing the time of wear and promoting ease of use. Multiple sizes of barrier strips can be placed on the card for utility in different applications such as handshakes, where a larger part of the palm needs to be protected and not just finger tips. A rough surface embossed or pasted on the card itself is used for removal of the barrier strips. All the above features offer an alternative to the existing inventions or methods and differentiate the Sanicard from other related inventions (Duffy, Timothy, US Patent 20090013441, 2007; Louise Taylor-Lopez, US Patent 20140331377, 2014).

The following list of relevant patents with a very brief description are referenced here. These inventions discuss the need for hygiene and are improvements or new complementary techniques for existing methods.

U.S. Pat. No. 5,636,406 issued to Strong, Vonda in the year 1997 describes a self-adhering lotion application pad for adhesive attachment to a human hand covering the palm, fingers and thumb against contact by lotion.

U.S. Pat. No. 6,178,554 issued to Pake, C. W. et al. in the year 1998 presents an easily removable mitt or pad worn on the palm till the wrist where the pad can be easily separated from the palm area beneath the user's hand.

U.S. Pat. No. 5,799,331 issued to Stewart, G. J. in the year 1998 relates to a dispensable easily engaged and released glove for protected manipulation of items. The low cost disposable hand protector provides a barrier between hand and an item being handled. The protector comprises of a thin contact sheet having overlying elements forming openings arrayed around a palm area for the fingers.

U.S. Pat. No. 6,243,868 issued to Wanzenreid, Ernest in the year 1999 presents a fingertip cover, a sleeve with an open and closed end that a user wears to protect finger tips. The fingertip protector is snugly secured to the finger by strips of hook and loop fastening material disposed about the circumference of the open end of the sleeve.

U.S. Pat. No. 6,647,549 issued to Jason McDevitt in the year 2003, describes the invention of a finger glove. The finger glove instead of fitting into the entire hand like a normal glove, is aptly designed to fit into a finger and can be used as a substitute for cotton balls, swabs and/or gauzes, or as an oral cleaning device. The glove can be partially made from texturized material having an abrasive surface useful for cleaning surfaces.

US Patent 20040083530 issued to LeVert Lisa et al. in the year 2004, presents finger and palm protector for public use. The invention is a shield with multiple finger sleeves and a palm shield. The sleeves are composed of hydrophobic polymeric or other materials coated or otherwise laden with disinfecting or pharmaceutical agents for destroying disease causing virus inter alia.

US Patent 20060059663 A1 issued to Angelo D'Ambrosio in the year 2006 presents a disposable hygienic door knob glove to specifically maintain sanitary conditions while using door knobs. The doorknob cover or shield is sized such that it offers a complete barrier between the skin of the palm and fingers of the hand and the surface of the door knob. The patent along with other related patent references use the approach of using disposable sheaths on the objects as opposed to protecting the skin of the individuals as with the present invention.

U.S. Pat. No. 8,684,228 issued to Kimberly Parker in the year 2009, is a self-containing sanitizing wipe dispensing system. It discusses cleanliness in relation to public health. The patent describes the spread of germs with examples and risks of infection due to improper practices of hygiene. The patent mentions some of the common limitations and practical issues associated with hand washing. It also references several other patents that mention the need for hygiene.

U.S. Pat. No. 8,294,585 issued to Paul Barnhill in the year 2012, describes a complete hand hygiene station and a method of monitoring a complete hand hygiene station. The station includes an automated wash cylinder, a sanitizer dispenser and a lotion dispenser.

U.S. Pat. No. 8,337,633 issued to Patrick Stine in the year 2012, describes a water-powered hand washing method. Routine hand washing with soap is often inadequate and can be complemented by other methods. The hand-washing system includes a work enclosure for containing one of the digits and a high-velocity, high-flow water spray during a washing operation.

U.S. Pat. No. 8,261,938 issued to Oradini Sr. and Michael, E. in the year 2012, discusses finger covers and use of finger cover dispensers. The finger covers referred to as mitts are protective sanitary coverings. The mitts and mitt dispenser are proposed as alternatives to finger gloves that can be cumbersome to put on and take off.

U.S. Pat. No. 8,602,257 B2860 issued to David Godsell in the year 2013, presents a multifunctional hand sanitizer where the hand sanitizer and hand wipes are used together indicating better hygiene practices using complementary approaches. The invention discloses a cup holder with partitioned compartments which provide access to various products such as hand wipes, sanitizing gel, lotion and similar components.

U.S. Pat. No. 8,695,152 issued to Marc Lemchen in the year 2014, describes an apparatus for cleaning the display surface of an electronic device such as cell phone or computer. The invention contains a wiper with a cleaner bar and cleaning fluid. The apparatus cleans the display surface after every use. The invention mentions how the surfaces can become unsanitary and the need to clean them.

U.S. Pat. No. 8,752,213 issued to Nancy Schrecongost in the year 2014, discusses a touchscreen-active protective covering for digit and dispensers. The utility of the invention is similar to some of the existing inventions but with focus on using the invention for touch screen devices.

US Patent 20140331377 issued to Louise Taylor-Lopez in the year 2014, presents a protective finger device for use with electronic devices. The invention is a finger covering to shield from germs and bacteria while using electronic devices.

US Patent 20140215676 issued to Calvin Jones in the year 2014, is a rubber tip finger attachment with small pin holes that is slid over the finger tip for use. It is a device called Licky Fingers. It is intended to be used by anyone that are in need of assistance of turning pages of boos, turning and handling sheets of paper, turning newspaper sheets or any other paper products by being able to wet the tips of fingers for a more firm grip. With the device there is no transfer of chemicals and germs to the mouth.

US Patent 20140078118 A1 issued to Robb, Stephen in the year 2014 is a hygienic finger protector includes a tubular sheath and an elastic stylus. The finger protector is designed to reach to approximately the first finger joint. The device is used to protect against contamination of germs.

U.S. Pat. No. 9,003,568 issued to Hofmeister, K. and Huneke, A. in the year 2015, describes a disposable glove made of two layers of thin plastic material. The glove has some useful features and is in a form that is comfortable to handle, small to pack and contoured correctly to one's hand.

CROSS REFERENCE TO RELATED APPLICATIONS

Some relevant products and procedures that offer hand hygiene and protection are listed here:

Hand washing with soap: Hand washing with soap is one of the widely used, relatively inexpensive and a best way to maintain hand hygiene. Soap is an excellent cleanser because of its ability to act as an emulsifying agent. An emulsifier is capable of dispersing one liquid into another immiscible liquid. Soap is made up of hydrophilic and hydrophobic components. The hydrophilic end has affinity to water and the hydrophobic part traps the dirt particles. Thus the drops are pulled off from the hands and washed off with water. Although uncommon, repeated use of some soap products may rarely cause irritation (Williams, C. et al. 2011).

Gloves: A glove is a garment covering the whole hand. Glovers have been used for several decades to protect hands while performing different tasks and also as a fashion addition. The tasks encompass daily physical activities such as protecting hands in gardening or specialized procedures such as surgery or laboratory experimentation. The gloves are commercially available in different shapes, sizes, material and there are different variations of the glove. The utility of gloves evolved over the years, and gloves are currently used for various purposes and different variations of the gloves were invented. Gloves which cover the entire hand or fist but do not have separate finger openings or sheaths are called mittens. Finger gloves that cover the finger have been used for cleaning purposes. Gloves protect and comfort hands against cold or heat, damage by friction, abrasion or chemicals and disease. They in turn provide a guard for what a bare hand should not touch. Latex, nitrile or vinyl disposable gloves are often worn by health care professionals as hygiene and contamination protection measures. While gloves offer protection in several instances and used to maintain hygiene in very filthy conditions, they are not worn in everyday life for routine tasks due to a few obvious reasons. Some of the reasons being they are not a part of the regular attire, they may be inconvenient and they may present the individual as the odd one out.

Hand sanitizer: A hand sanitizer or hand antiseptic is an interim supplement or alternative to hand washing with soap and water. Many preparations of hand sanitizers are commercially available in the form of gel, foam and liquid solutions. The active ingredient in hand sanitizers may be isopropanol, ethanol, n-propanol, or povidone-iodine. In the recent years, hand sanitizer has become a popular way to prevent spread of microorganisms thereby preventing diseases. Hand sanitizers are available in various places, can be easily purchased and are relatively inexpensive. However, the effect of the hand sanitizer lasts for short periods of time. Unlike the glove, the hand sanitizer does not prevent direct contact with particles such as microbes, body fluids or any other filthy or harmful substances. Furthermore, the hand sanitizers being of chemical nature pose the routine disadvantages of regular use of chemicals with skin including harming the beneficial bacteria that reside on the body.

Sanitizing wipes: Sanitizing wipes which are pre-moistened wipes with disinfectant are also gaining popularity. The wipes are easily portable and can be used to clean hands or surfaces of personal objects. Occasional wiping of objects in public places may be possible. The use of such wipes for baby care has been in practice for several years but their use in daily life is relatively less. A variety of inventions along the lines of types of wipes, and containers to hold the wipes also exist (Arians, Michael, U.S. Pat. No. 4,644,689, 1987).

Wound hygiene and bandages: Bandage is a piece of material used as a dressing usually to protect a wound and maintain wound hygiene. Adhesive bandages help in adhering to skin and are known by their generic trade mark band-aid. The adhesive bandages protect the wound or cut from bacteria and exposure thereby allowing the body to undergo the healing process. The adhesive bandages have several variants and come in different shapes, sizes and colors. The bandages are used to maintain the wound hygiene but are not practiced in everyday life for routine skin hygiene.

SIGNIFICANCE OF THE CURRENT INVENTION

Hygiene and cleanliness is important in daily lives and even more important in circumstances where individuals are exposed to harmful substances or organisms. Several hygiene monitoring methods are reported to monitor the extent of cleanliness (William, C. K. and Carnahan, 2013). Every day we all get exposed to a variety of unhygienic or even harmful particles that reside on object surfaces. Some common examples include use of shopping carts which have been used by others, computer keyboards, door handles, touch screens, toilet seat covers, television remotes, vending machines, door knobs, handshakes etc. All these surfaces harbor a variety of germs or unhygienic substances. In general there are three major modes of external transfer of particles from one individual to another, via air, water or direct contact. Several preventative measures for each of the three modes of transmission exist. Some of the popular measures include washing procedures, wearing masks, sterilization procedures, wearing gloves, hand sanitization and so on. The invention described here is more relevant to offering protection from transfer of particles via physical contact mode by skin, in specific skin of palm, in a simple card format. The invention complements the existing methods and differentiates itself in some respects attempting to address limitations of the existing methods and inventions.

Common everyday activities include but are not limited to use of key boards of electronic devices, handshakes, door knobs etc. The ease of use (wear and removal), transportability facilitates utility of the product in situations where other common methods may not be readily used. Serving as a barrier between the skin and object at main contact points significantly minimizes direct contact with dirt and germs thereby potentially reducing the spread of infections.

BRIEF DESCRIPTION AND SEVERAL VIEWS OF DRAWING OF THE INVENTION

Figure 1:
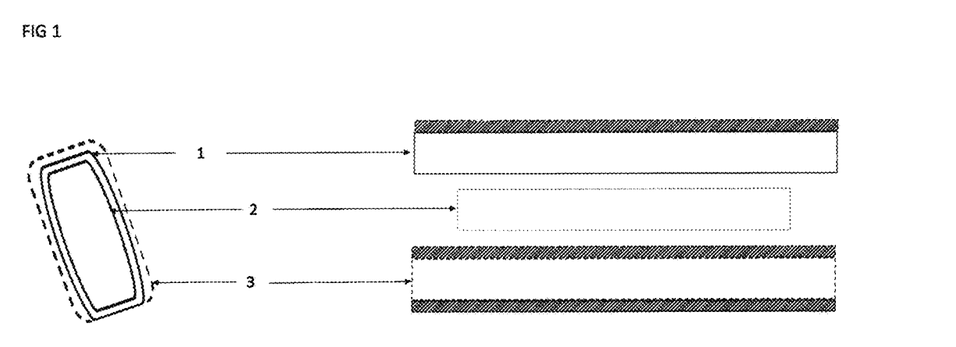
FIG. 1 is a pictorial representation of the adhesive card barrier assembly module. The top layer (1), is the barrier strip with adhesive side facing upward. The middle layer (2) is a colored paper cutout. The bottom layer (3) is a dual adhesive sheet.
Figure 2:
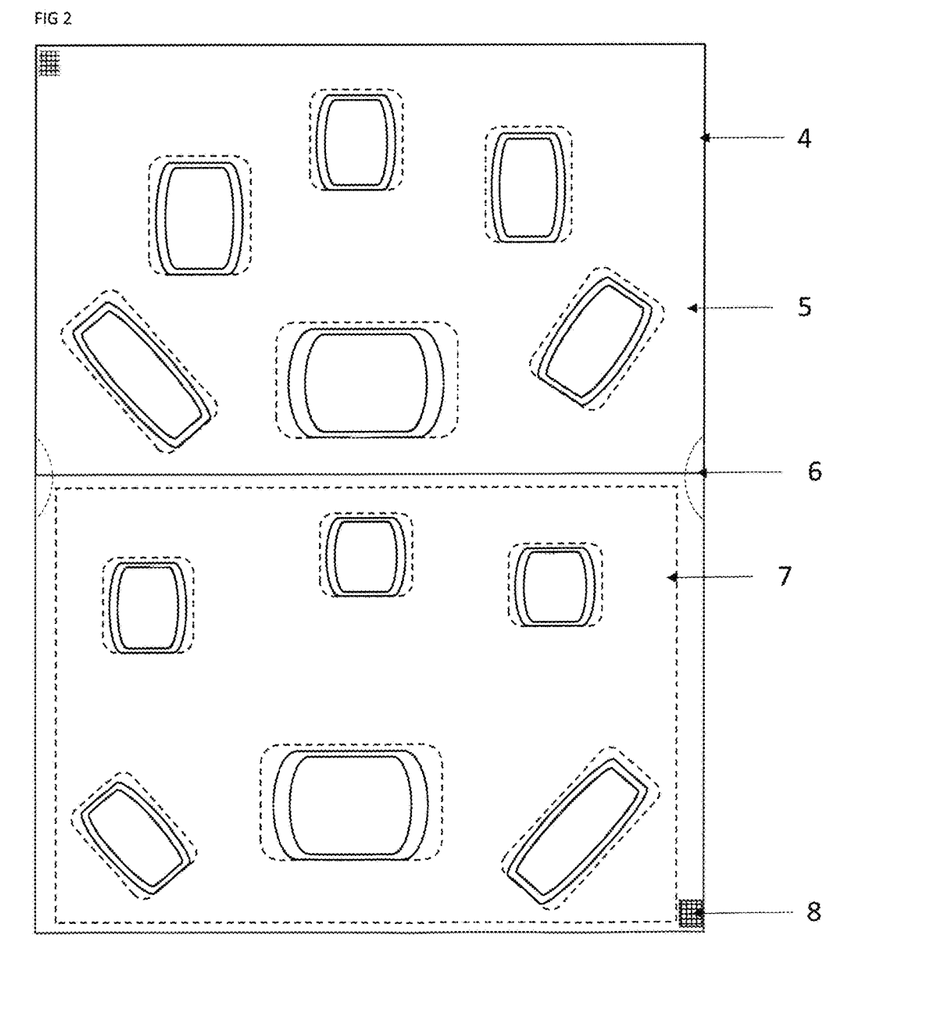

In order to offer optimum protection and yet address the deficiencies of existing methods, some of the below experiments have been conducted. FIGS. 1 and 2 show the invention which is an assembly of adhesive sheets and a porous barrier strip suitable for ready wear.

Figure 3:
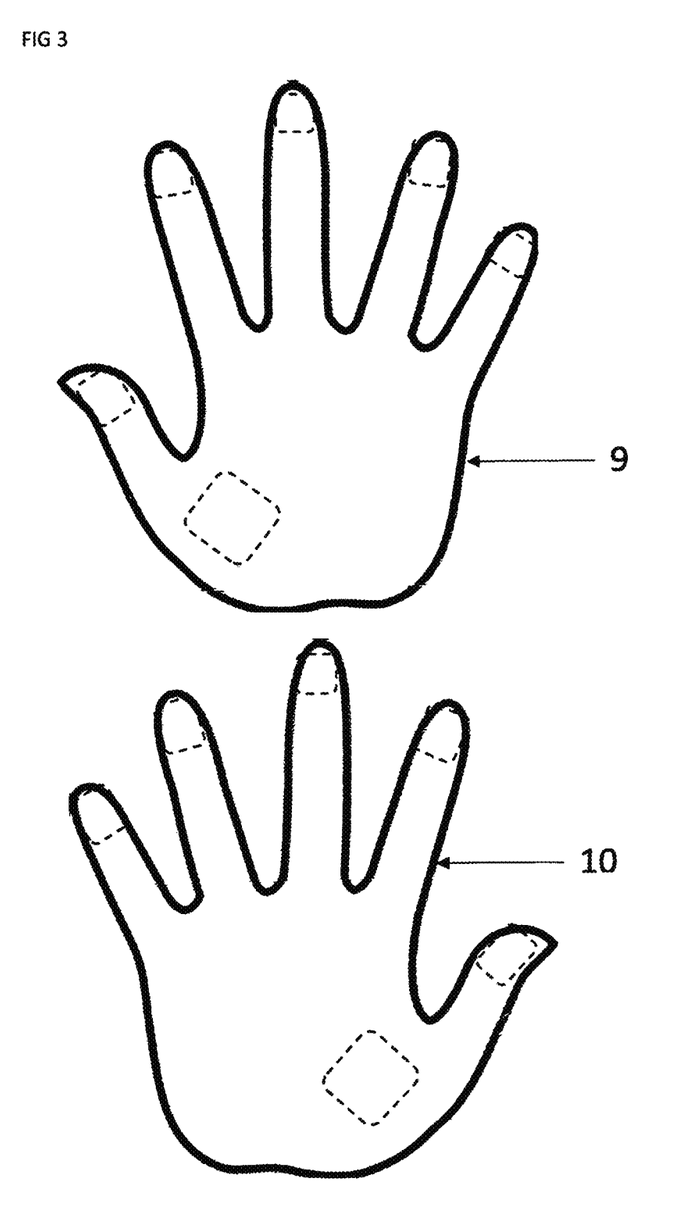
FIG. 3: A pictorial representation of left (9) and right (10) palms wearing barrier strips.

Hands after wearing the barrier strips is shown in FIG. 3. This figure is an example of a card that can be used for computer key boards. The barrier strips are worn at major contact points including finger tips and bottom region of the thumb.

Process steps that lead to the design and optimization of the Sanicard: There are several aspects that need to be considered before designing a proper tool for the proposed utility of maintaining hygiene. The below experiments were conducted for utilizing the product for computer key board hygiene. The schema of experiments for other uses follows a similar design of experiments. Some of the following experiments are briefly discussed.

a) Determining contact points. One of the initial aspects before designing the appropriate Sanicard is to determine which points on the palm or skin are more prone to contact with objects. In order to determine the contact points various impressions were taken and compared before and after contact with barrier strips.

b) Determining the optimum size and shape of the contact points: Determining the optimum size and shape of the contact points is another important aspect. The objective of this determination is to design a small and optimum shape of the barrier to maintain minimum visibility upon wearing. Size and shape are determined by analyzing impressions obtained before and after use of the Sanicard prototypes.

c) Texture and feel of barrier strips: Since an adhesive part is being on the skin, it is necessary to ensure that the comfort. Some cardinal properties that differentiate the use of barrier strips from gloves or bandages are smaller size, minimal feel and visibility, porousness and transportability.

d) Determining the appropriate material for the card barrier assembly. Material used in the Sanicard embodiment is important for a variety of reasons. Some of the desirable features include breathability, less absorbing capacity, easy to wear and remove, minimal visibility.

e) Optimizing the barrier strips to palm sizes: Palm sizes and contact points vary across individuals. Impressions of various palm sizes from normal individuals including both male and females have been used for product improvements.

Some Current Limitations of The Sanicard Invention

The invention is designed to address the need for hygiene and provides partial protection from direct contact with particles. Similar to other available products the invention complements other methods but cannot be the only measure to offer complete hygiene. In fact using this invention along with other approaches can be more effective. The contact points are identified by studying most routine operations of the palm. The dimensions of the barriers are optimized for average palm sizes. Palms that are widely deviant from normal palms may need customization. The invention is not designed for wear over wounds or skin with abrasions.

Seasonal And Location Based Utility Of The Invention

The invention finds utility in public places where objects are used by several individuals. Similar to hand sanitizers, the invention could be more beneficial in climates or seasons where the incidence of disease causing microbes are more prevalent. It is also possible that the invention could be more beneficial at regions that may have higher concentration of microbes. Furthermore, in households with children who often bring home germs, adults also contribute significantly in transfer of particles across objects and people. This contribution can potentially be minimized by this invention.

DETAILED DESCRIPTION OF THE INVENTION

The invention is a paper based card (referred to as Sanicard) comprising of an assembly of adhesive sheets and a micro or nano porous barrier strip that minimizes direct contact of the skin with objects or skin of individuals. The assembly helps in easy wear and removal of the barrier strips on parts of a palm or other parts of the skin. The wear of the strip leads to offering protection by minimizing contact with particles such as body fluid droplets/dust/microbes that commonly reside on objects thereby maintaining hygiene. The function of the porous barrier strip is analogous to the function of a normal membrane. The pores are preferably enough for the skin to breathe but not big enough for the particles to pass through.

Several major contact points of the palm that come in contact with objects in routine tasks have been experimentally determined by creating and measuring the impressions. Based on the average shape of the impression, thin transparent barrier strips were cut out. The strips were placed on a base adhesive sheet. FIG. 1 shows the order of arrangement of components. A dual adhesive base sheet is placed on a paper card. A colored paper cutout is placed on the adhesive base sheet. A one side adhesive porous barrier strip that is slightly larger in all dimensions than the colored cutout is placed over the colored cutout with the adhesive side facing upwards. A wax paper is placed over the strip to preserve the adhesive property when the strip is stored. FIG. 2 is a representation of a typical Sanicard. The user simply places his/her plams on the card to wear the strips. The colored cutouts on the card guides the palm to be positioned appropriately. They also prevent the barrier strips from completely adhering to the dual adhesive sheet. The palm can be positioned in different ways with some or all the finger digits in a convenient manner. The strips immediately adhere to the palm (FIG. 3). The strips can be removed by rolling gently over a rough surface, peeling or washing. The Sanicard also contains a rough surface for easy removal. The Sanicard which is approximately the size of a small card is easy to carry.

Material used in the invention: The adhesive card, color paper, card boards are available as general stationery in stores. Different commercially available barrier strips were tested to choose the appropriate material for this invention. The strips are positioned such that they adhere to the card (that serves as a strip holder) and attach to the palm when compressed against the card. The strips are typically polymers that are commonly used in other applications. Various types of material can serve as the strip, some key features such as porous nature, transparent, minimal visibility, leaving minimal adhesive on skin were taken into consideration for the utility of this invention. The properties of the material also add benefit to the invention by preventing certain special types of microorganisms (Moore, G. et al. 2013).

Figure 4:
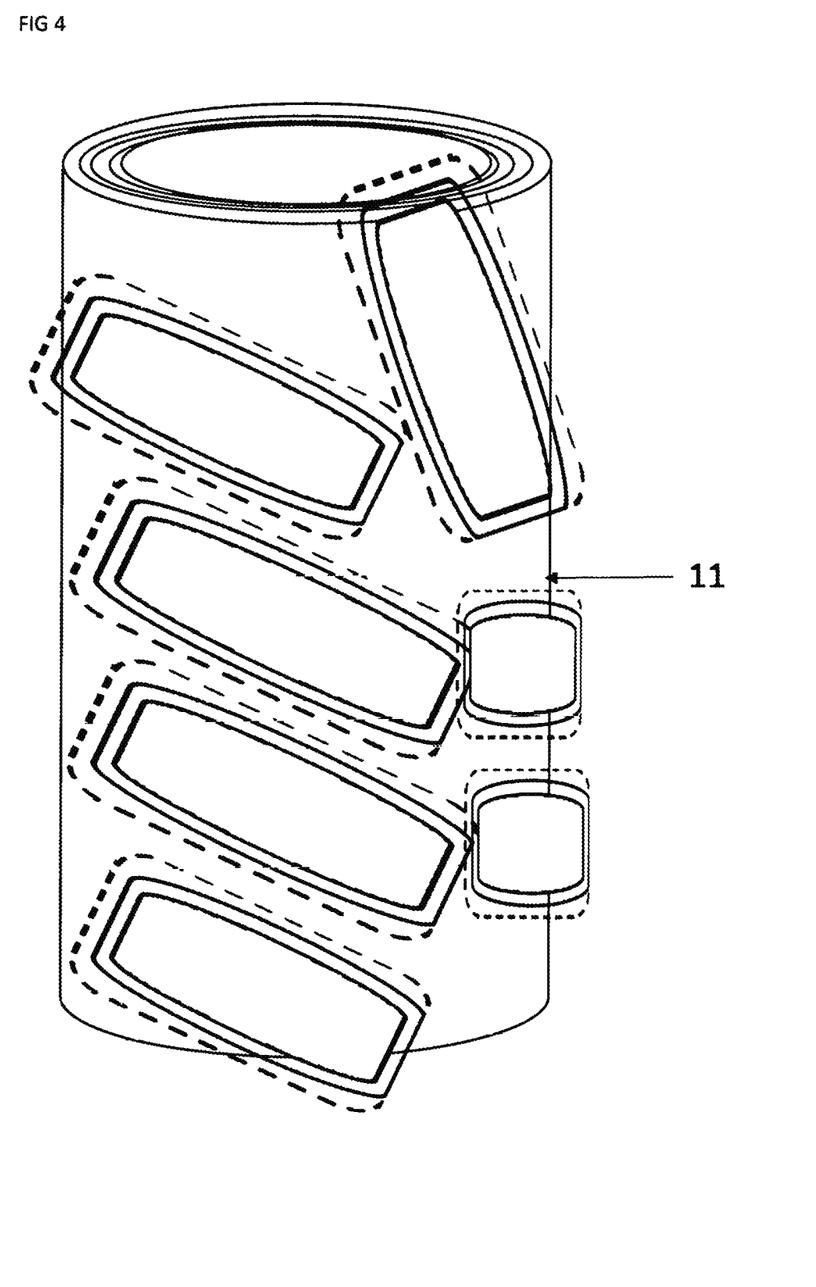
FIG. 4: A pictorial representation of the card barrier assembly in a cylindrical cardboard format (11). The product in this case is a cylindrical structure onto which the adhesive-sheet-barrier assembly is positioned appropriately. Only some modules are shown in this view. The assembly is covered with a wax paper. The user removes the wax paper and positions the hand. Multiple rolls of the assembly can be placed on the cylindrical platform.
Figure 5:
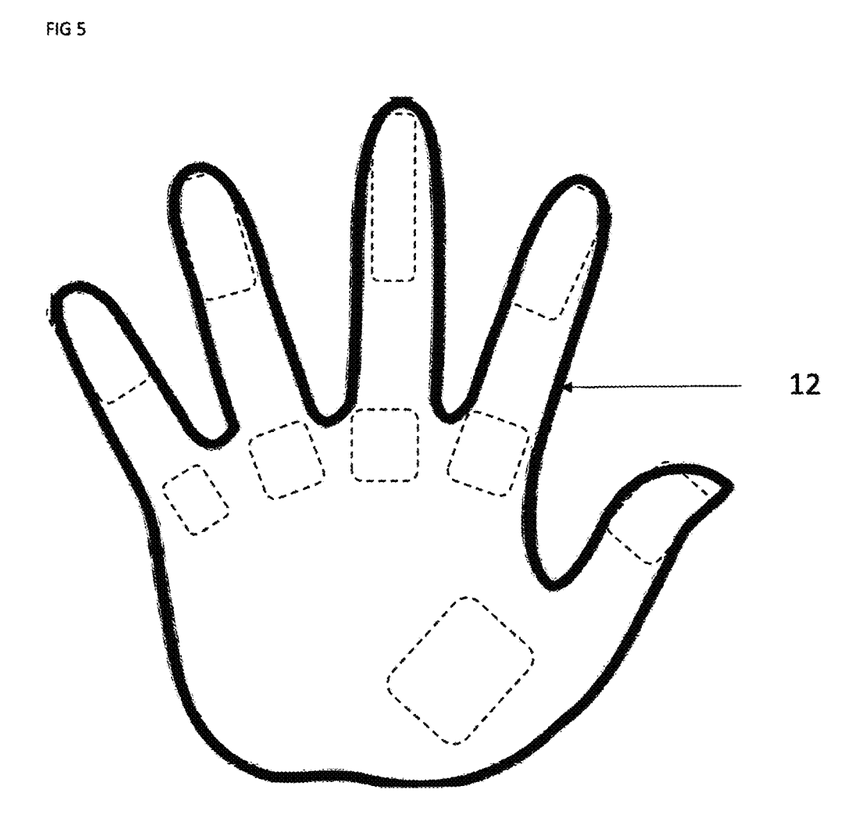
FIG. 5: A pictorial representation of right (12) palm wearing barrier strips. It is intended for utility in handshakes.
Figure 6:
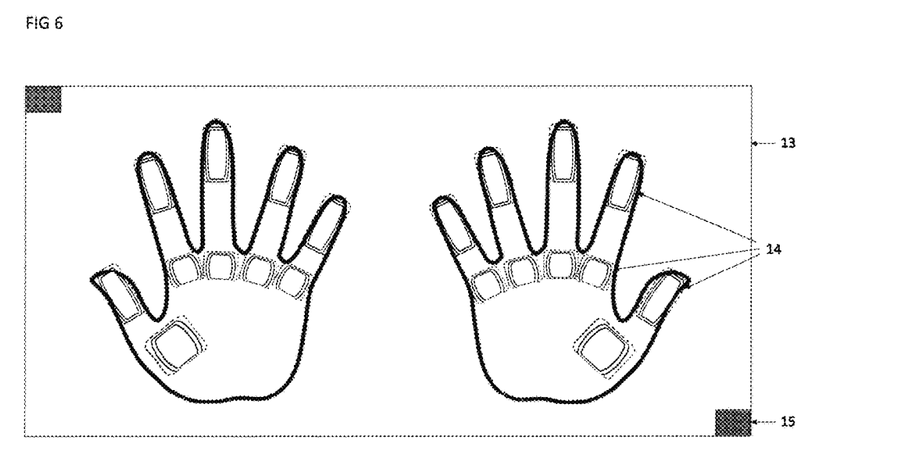
FIG. 6: A pictorial representation of the card barrier assembly in a larger flat format (13) with adhesive-sheet-barrier assemblies (14) placed on a drawing of the palm at appropriate contact points. The user positions his/her palms on the card barrier assembly palm drawings and presses his/her hand to wear the barrier strips. A rough surface on the card (15) is used for easy removal of the strips.

Depending on the specific use, the invention may be assembled differently or available in a different shape and form, albeit serving a similar utility. A Sanicard utilized for computer keyboard has a different sized elements from a Sanicard utilized for handshakes. The mode of wear may also be different for a different utility. For example, use of a cylindrical structure for assembly in lieu of a card is shown in FIG. 4. The principle is similar to what is shown in FIG. 1, but in this case the strips are assembled on a cylindrical structure instead of a flat surface. The barrier strips adhere to the key points of the palm after the palm holds the cylinder (FIG. 5). In another embodiment, a larger card containing drawings of a palm with card barrier assembly at relevant points is shown (FIG. 6).

Examples of key applications of the invention

Minimizing contact with particles and maintaining hygiene is always necessary and the invention can be used in such situations. Two routine applications are discussed below to show the utility of the product.

a) Use of the invention on computer keyboard/screen/mouse: Use of computers and other smart devices via keyboards, mouse and touch screen has become the norm in our lives. Computer keyboards and screens in common places are touched by multiple individuals and harbor numerous dust particles and germs. Reports showed that the microbes on the keyboards are several folds higher than those found on toilet seats (Andersen, G and Palombo, E. A. 2009). Computer keyboard covers with antimicrobials were reported (D"Antonio, N. N. 2013). Some computer keyboard users often use their fingers to eat and touch body parts and use the keyboards Sarah Miller et al. from National Center for Health Research reported the types of bacteria found on keyboards tend to live on people (skin, mouth, nasal passages). Thus the keyboard and other allied accessories become a home for dirt and microbes. The cheapest and common ways to minimize contact from these microbes are repeated washing of hands or periodic cleaning of keyboards/screens. However there are limitations to these approaches. Washing hands just before use of computers or touch screens in public places is often not possible. Moreover, while cleaning personal computer keyboards or covering them is feasible but cleaning computer keyboards and other devices in public places that belong to other providers are not readily feasible. Keyboards and touchscreens used in public places are heavily used and cleanliness of these items is beyond the control of an individual user. Thus protecting one's Own self is more practical, and the current invention offers some benefit in these situations.

b) Use on routine handling or interaction between individuals and/or objects: Door handles, handshakes etc are tasks where the skin of palms comes in direct contact with objects. All these objects are usually touched by different individuals and harbor particles of different nature. The unhygienic practices of one individual can affect the other individuals. The common way of protecting from these particles is by use of gloves, hand sanitizers or washing hands periodically. The invention helps here by complementing these approaches and minimizing the spread of particles and contaminants.

REFERENCE

1. Williams, C. K. and Carnahan, H. Development and validation of tools for assessing use of personal protective equipment in health card. Am J Infect Control, 2013, 41(1), 28-32.
2. Elaine, L. Skin hygiene and infection prevention: More of the same or different approaches? Clin Infect Dis, 1999, 29(5), 1287-1294.
3. Williams, C. et al. The use of a measure of acute irritation to predict the outcome of repeated usage of hand soap products. Br J Dermatol., 2011, 164(6), 1311-1315.
4. Moore, G. et al. The effect of glove material upon the transfer of methicillin-resistant *Staphylococcus aureus* to and from a gloved hand. Am J Infect Control. 2013, 41(1), 19-23.
5. Anderson, G. and Palombo, E. A. Microbial contamination of computer keyboards in a university setting. Am J Infect Control. 2009, 37(6), 507-509.
6. D'Antonio, N. N. et al. Computer keyboard covers impregnated with a novel antimicrobial polymer significantly reduce microbial contamination. Am J Infect Control 2013, 41(4), 337-339,
7. Sarah, R. N. Are there more bacteria on computer keyboards than toilet seats? National Center for Health Research, the voice of prevention, treatment and policy, August 2010.

BRIEF DESCRIPTION OF DRAWINGS

FIG. 1: FIG. 1 is also shown as a side view in a stacked format with adhesive side or sides is shown by striped lines.

FIG. 2: FIG. 2 is a pictorial representation of the card barrier assembly. Several barrier assembly modules as shown in FIG. 1 are positioned on a paper based card (4) at desired places to form the article. The dual adhesive sheet (3) from FIG. 1 attaches to the card. The arrangement of the adhesive card barrier assembly (5) in this card is intended for utility on computer keyboards. The foldable section of the card (6) is indicated. A wax paper (7) is placed over the modules and in this case serves the purpose of covering for two articles simultaneously. A rough surface on the card (8) is shown.

The invention claimed is:

1. A disposable article for application of one or more barrier strips onto skin, comprising: a) a card made of paper; b) dual adhesive sheets; c) colored paper cutouts with smaller dimensions than the dual adhesive sheets; d) microporous barrier strips of measured dimensions with adhesive on one side and e) wax paper, stacked in order a, b, c, d and e.

2. The article in claim 1 wherein one side of the dual adhesive sheet adheres to the said card and the other side adheres to the said colored paper cutouts and along the perimeter of the non-adhesive side of the said microporous barrier strip.

3. The article in claim 1 wherein said card is flat or cylindrical in shape.

4. The article in claim 1 wherein the article is stacked.

5. The article in claim 1 wherein the said card contains a rough or embossed surface to remove the worn barrier strip by rolling skin against said surface.

6. Utility of article in claim 1 to minimize the transfer of particles across individuals or from objects to individuals in daily activities.

7. In another embodiment the card device in claim 1, wherein the said barrier strips are used as a means to minimize unhygienic habits commonly associated with fingers via using barrier strips with added fragrance and taste.

8. In another embodiment the card device in claim 1, wherein the said barrier strips are used to prevent spread of microbes via using barrier strips with antiseptic properties.

* * * * *